(12) United States Patent
Dam-Huisman

(10) Patent No.: US 9,861,448 B2
(45) Date of Patent: Jan. 9, 2018

(54) ASSEMBLY FOR PROTECTING AND CLEANING A MEDICAL INSTRUMENT

(71) Applicant: CREA IP B.V., Dordrecht (NL)

(72) Inventor: Adriaantje Coliene Dam-Huisman, Delft (NL)

(73) Assignee: CREA IP B.V., Dordrecht (NL)

( * ) Notice: Subject to any disclaimer, the term of this patent is extended or adjusted under 35 U.S.C. 154(b) by 0 days.

(21) Appl. No.: 14/968,327

(22) Filed: Dec. 14, 2015

(65) Prior Publication Data

US 2017/0165022 A1 Jun. 15, 2017

(51) Int. Cl.
*A61J 1/00* (2006.01)
*A61B 50/30* (2016.01)
*A61B 90/70* (2016.01)

(52) U.S. Cl.
CPC .............. *A61B 50/30* (2016.02); *A61B 90/70* (2016.02); *A61J 1/00* (2013.01); *A61B 2050/3008* (2016.02)

(58) Field of Classification Search
CPC . A61B 50/30; A61B 90/70; A61B 2050/3008; A61J 1/00
USPC .............................. 134/116, 166 R, 198, 201
See application file for complete search history.

(56) References Cited

U.S. PATENT DOCUMENTS

| 2008/0188877 A1 | 8/2008 | Hickingbotham |
| 2008/0199356 A1* | 8/2008 | Suter .................... A61C 19/002 422/28 |

* cited by examiner

*Primary Examiner* — Levon J Shahinian
(74) *Attorney, Agent, or Firm* — Young & Thompson

(57) ABSTRACT

An assembly for protecting and cleaning a medical instrument having an operational part and a hand grip part. The assembly has a protection element with cooperating retention parts for fixing the hand grip of the medical instrument in the protection element. A cavity is formed by a wall for protecting the operational part of the medical instrument. The assembly further has a cleaning assist element with a tubular shape and being fixable to the wall of the protection element.

17 Claims, 3 Drawing Sheets

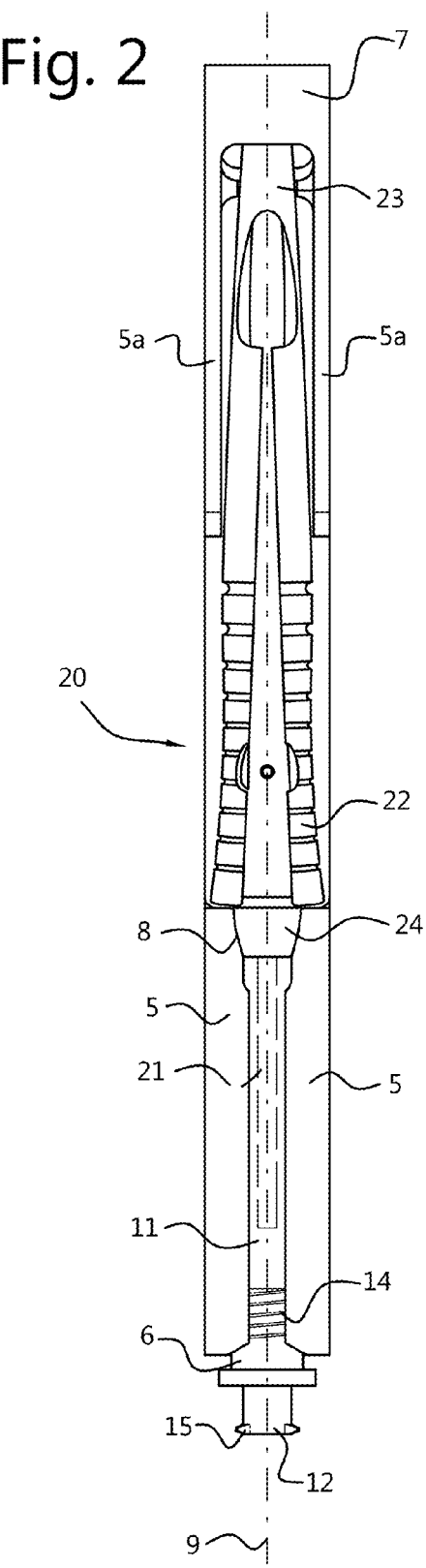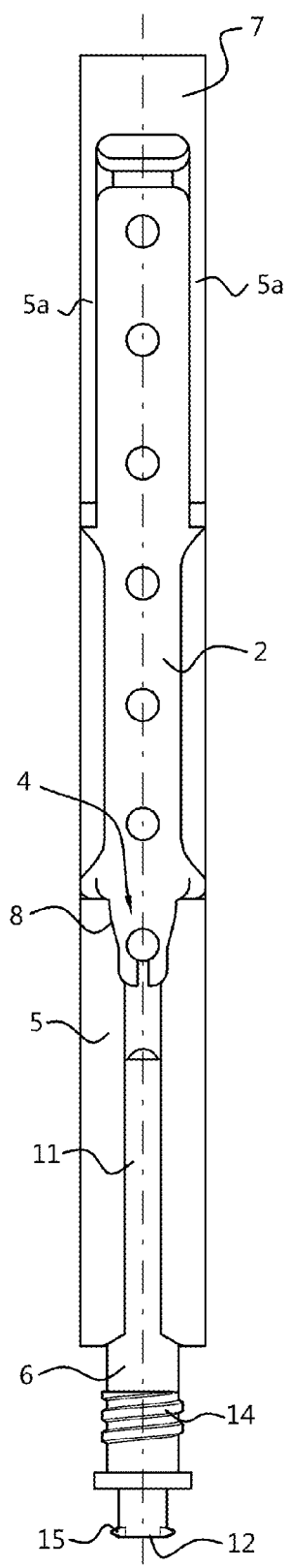

ASSEMBLY FOR PROTECTING AND CLEANING A MEDICAL INSTRUMENT

FIELD OF THE INVENTION

The present invention relates to an assembly for protecting and cleaning a medical instrument for ophthalmological applications, such as a vitreoretinal instrument.

PRIOR ART

US patent publication US 2008/0188877 discloses an instrument set for removing an object from the eye including a forceps having first and second jaws mounted for relative movement toward and away from one another for closing and opening the first and second jaws. The instrument may further comprise a jaw shaft extending through an elongated sleeve, wherein the jaw shaft is provided with the first and second jaws at an end part thereof. The first and second jaws can be opened or closed through relative axial movement between the jaw shaft and sleeve. In an embodiment, the forceps may be made primarily of inexpensive materials and moldings to reduce the instrument cost to allow the instrument to be disposable. In a further embodiment, the forceps may be packaged in a single procedure pack enclosing the forceps in a closed sterile environment.

A medical instrument such as a forceps disclosed above is typically packaged in a sterile environment and made to be used only once during a procedure and disposed afterwards, so that a newly packaged sterile medical instrument can be used for a subsequent procedure. However, disposable medical instruments tend to increase medical costs and generate a relatively large amount of waste material.

SUMMARY OF THE INVENTION

The present invention seeks to provide an assembly for protecting, storing, and cleaning a medical instrument having an operational part and a hand grip part, wherein the assembly not only provides protective storage for the medical instrument but also allows the medical instrument to be used multiple times and guaranteeing sterility between subsequent procedures. The assembly of the present invention may be adapted for protecting and cleaning an ophthalmological instrument, such as a vitreoretinal forceps and the like.

According to the present invention, an assembly of the type defined in the preamble is provided, comprising a protection element having cooperating retention parts for fixing the hand grip of the medical instrument in the protection element, and a cavity formed by a wall for protecting the operational part of the medical instrument, and a cleaning assist element having a tubular shape and being fixable to the wall of the protection element.

The assembly of the present invention allows a delicate medical instrument, such as an ophthalmological instrument, to be conveniently cleaned and/or sterilized while being stored in a protective housing. The medical instrument need not be configured for a single procedure and can be made to last for multiple procedures, thereby allowing for medical instrument designs of a higher quality, durability, precision, usability etc.

SHORT DESCRIPTION OF DRAWINGS

The present invention will be discussed in more detail below, using a number of exemplary embodiments, with reference to the attached drawings, in which FIG. 1 shows a three dimensional view of an embodiment of a protection element as used for the assembly according to the present invention;

FIG. 2 shows a top view of an embodiment of a medical instrument stored in an assembly according to the present invention;

FIG. 3 shows a top view of an embodiment of an assembly according to the present invention without a medical instrument;

Figure 4:
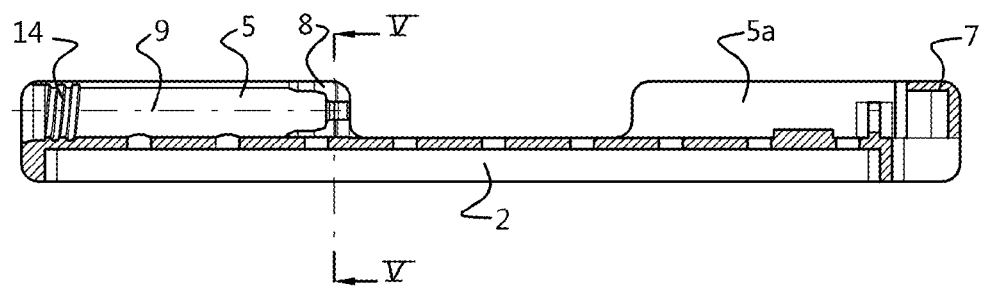
Figure 5:
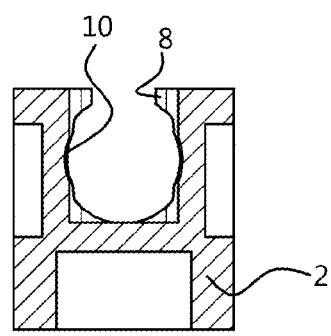
Figure 6:
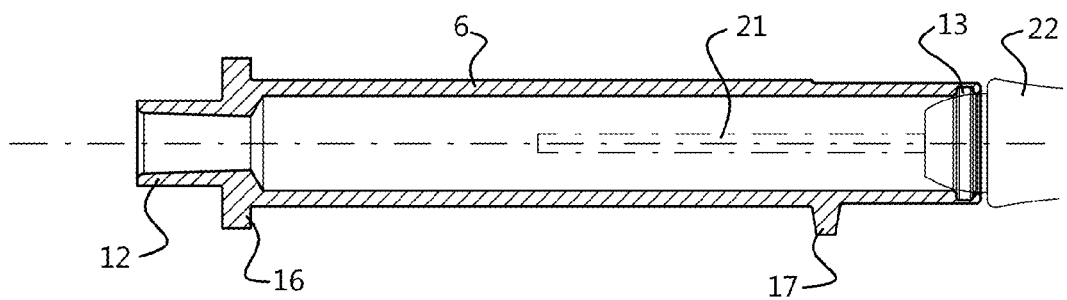

FIG. 4 shows a cross sectional view of an embodiment of a protection element as used for the assembly according to the present invention; and FIG. 5 shows a cross sectional view of a clamping element as used for the assembly of FIG. 4 along the lines V-V; and FIG. 6 shows a cross sectional view of an embodiment of a cleaning assist element as used for the assembly according to the present invention.

DETAILED DESCRIPTION OF EXEMPLARY EMBODIMENTS

Figure 1:
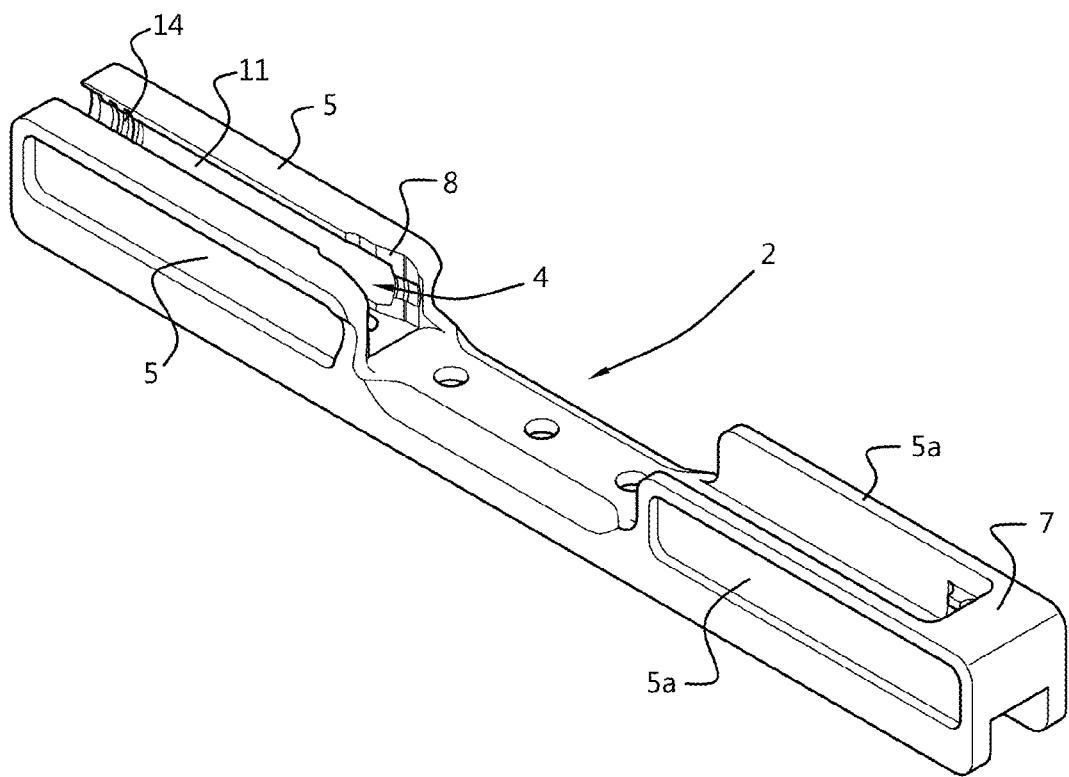

FIG. 1 shows a three dimensional view of an embodiment of a protection element as used for the assembly according to the present invention, where FIG. 2 shows a top view of an embodiment of a medical instrument stored in a protection element forming the assembly.

In the embodiments shown, the assembly of the present invention is designed and arranged to house a medical instrument 20 having an operational part 21 (dotted line in FIG. 2) and a hand grip part 22, wherein the hand grip part 22 has a proximal end 24 and a distal end 23. In a group of embodiments the medical instrument 20 may be an ophthalmic or ophthalmological instrument, e.g. a vitreoretinal instrument and in particular a vitreoretinal forceps and the like.

The assembly comprises a protection element 2 having cooperating retention parts for fixing the hand grip part 22 of the medical instrument 20 in the protection element 2. The cooperating retention parts are typically arranged for releasably affixing the hand grip part 22 of the medical instrument 20 in the protection element 2 yet prevent spontaneous release of the medical instrument 20 when the assembly is, e.g., being carried by a user.

There is further provided a cavity 4 formed by a wall 5 for protecting the operational part 21 of the medical instrument 20. The wall 5 encloses, at least in part, the operational part 21 for optimal protection. The assembly further comprises a cleaning assist element 6 having a tubular shape, wherein the cleaning assist element 6 is fixable to the wall 5 of the protection element 2. The combination of retention parts, wall 5 and cleaning assist element 6 allows for a proper alignment of the medical instrument 20 (along the longitudinal axis 9 as shown in FIG. 2).

An advantage of the assembly of the present invention is that a medical instrument 20 and in particular a delicate medical instrument 20 can be stored and cleaned in a protective fashion through the cleaning assist element 6, wherein the operational part 21 is receivable in the cleaning assist element 6 which is operable to e.g. sterilize the operational part 21 for a subsequent procedure. It is therefore not needed to utilize inexpensive materials and/or moldings to reduce instrument costs, so that the medical instrument 20 can be designed to primarily satisfy quality and reliability requirements instead of rendering it disposable for a single procedure.

In an embodiment, the retention parts comprise a fixing holder 7 for a distal end 23 of the hand grip part 22 of the medical instrument 20, and a clamping element 8 for a proximal end 24 of the hand grip part. The fixing holder 7 and the clamping element 8 each allow for a releasable connection and placement of the medical instrument 20 into the protection element 2 by, e.g., manually pushing, pulling and/or sliding the medical instrument 20 into and out of the fixing holder 7 and/or clamping element 8.

In a further embodiment, the fixing holder 7 may alternatively or additionally comprise one or more holder walls 5a enclosing, at least in part, the distal end 23 of the medical instrument 20. The one or more holder walls 5a provide protection to the distal end 23 as well as lateral stability. In a further embodiment the one or more holder walls 5a may be resilient holder walls 5a for providing further clamping engagement with the medical instrument 20 and in particular with the distal end 23 thereof, so that a further and/or alternative releasable connection between the medical instrument 20 and the protection element 2 is obtained.

In an embodiment, the cavity 4 formed by the wall 5 is congruent with the tubular cleaning assist element 6, allowing congruent engagement between the cleaning assist element 6 with the cavity 4 for optimal but releasable connection of the cleaning assist element 6 to the protection element 2. In an exemplary embodiment, the cavity 4 is a cylindrical cavity with a longitudinal axis 9, where the cavity 4 provides longitudinal and lateral alignment of the cleaning assist element 6 relative to the protection element 2. This embodiment ensures that, for example, an elongated and relatively thin operational part 21 need not come into contact with the cleaning assist element 6 when it is affixed to the protection element 2, preventing possible bending stresses on the operational part 21. Also, for sterility and cleaning requirements, contact of the operational part 21 with the cleaning assist element 6 should be avoided, which is possible by the alignment between the medical instrument 20 and the cleaning assist element 6 arranged on the protection element 2.

In an advantageous embodiment the cavity 4 comprises a longitudinal slit or cut-out 11. For example, the wall 5 of the protection element 2 may define a longitudinal slit or cut-out 11 along the longitudinal axis 9, so that the wall 5 encloses at least in part the cleaning assist element 6 when it is affixed to the protection element 2. The longitudinal slit 11 allows convenient placement of the operational part 21 of the medical instrument 20 in the protection element 2. For example, a vitreoretinal forceps may comprise a relatively thin and elongated operational part 21 for insertion into an eye. The longitudinal slit 11 then allows unimpeded placement of the operational part 21 into the protective element 2, preventing any contact between the operational part 21 and the wall 5.

FIG. 3 shows a top view of an embodiment of an assembly according to the present invention, before placement of a medical instrument 20. In the embodiment shown, the cleaning assist element 6 may comprise a fluid coupling element 12, which allows a cleaning medium to be injected into and/or removed from the cleaning assist element 6, such as sterilizing agent. In an advantageous embodiment, the fluid coupling element 12 may comprise a tube coupling, so that standard tubes, hoses or lines known to the medical industry can be used conveniently for connection to a cleaning medium. In a specific embodiment the fluid coupling element 12 may comprise a Luer fitting. An advantage of the Luer fitting is that a standard fluid tube, hose or line can be used for making a leak-free connection with the cleaning assist element 6 without using a hose clamp or hose clip and the like as a mere tapered interference fit is established between the fluid tube and the Luer fitting The cleaning assist element 6 can therefore be quickly connected to, for example, a cleaning source dispensing a sterilizing agent.

In light of the invention, the tubular shape of the cleaning assist element 6 allows easy insertion of the cleaning assist element 6 into the cavity 4. To affix that cleaning assist element 6 to the protection element 2, there is provided an embodiment wherein the cleaning assist element 6 is arranged for clamping engagement with the wall 5 of the protection element 2, wherein an adequate and sufficient interference fit can be established for affixing the cleaning assist element 6 to the protection element 2.

As further depicted in FIG. 3, in an embodiment the protection element 2 and cleaning assist element 6 are attached using a screw coupling 14. So the cleaning assist element 6 may be threaded onto or into the protection element 2, which allows not only the cleaning assist element 6 to be secured to the protection element 2, but an insertion depth of the cleaning assist element 6 into the cavity 4 can be controlled through, for example, a lead and/or pitch of the screw coupling, wherein the lead and/or pitch of the screw thread of the screw coupling determines a linear distance and thus insertion depth over which the cleaning assist element 6 travels in one revolution thereof.

FIG. 4 shows a cross sectional view of an embodiment of a protection element 2 as used for the assembly according to the present invention. In the embodiment shown, the screw coupling 14 and its screw thread are clearly visibly whereby the cleaning assist element 6 can be affixed to the protection element 2 and whereby a desired insertion depth is obtained by rotating the cleaning assist element 6 by a number of revolutions thereof. The screw coupling 14 can be provided with any suitable screw type and lead, in order to meet requirements for the protection and cleaning of the medical instrument 20.

As mentioned earlier, the fixing holder 7 and the clamping element 8 of the retention parts each allow for a releasable placement of the medical instrument 20 into the protection element 2. For example, FIG. 5 shows a cross sectional view of a clamping element as used for the assembly of FIG. 4 along the lines V-V. In the embodiment shown, the clamping element 8 may comprise an inner clamping surface 10. The inner clamping surface 10 provides clamping engagement between the medical instrument 20, in particular the proximal end 24 thereof, and the wall 5 of the protection element 2. In an embodiment, the inner clamping surface 10 may further comprise a tapered clamping surface providing a tapered fit between the proximal end 24 of the medical instrument 20 and the wall 5 of the protection element 2.

According to the present invention, the tubular shaped cleaning assist element 6 allows for e.g. protective storage and convenient sterilization of the medical instrument 20, particularly with respect to a delicate operational part 21 thereof. As a result the medical instrument 20 need not be a disposable article but can be designed as a multiple procedure medical instrument. To ensure that reliable cleaning and sterilization of the medical instrument 20 can be achieved, adequate sealing engagement between the cleaning assist element 6 and the medical instrument 20 must be guaranteed.

To further clarify on how reliable cleaning and sterilization can be achieved, FIG. 6 shows a cross sectional view of an embodiment of a cleaning assist element as used for the assembly according to the present invention. In the embodiment shown, the cleaning assist element 6 may comprise a sealing element 13 (e.g. an O-ring), which is arranged to seal the operational part 21 of the medical instrument 20 inside the cleaning assist element 6 during operation. In particular, the cleaning assist element 6 may comprise a cleaning cavity operable to receive the operational part 21 of the medical instrument 20. The sealing element 13 then provides a leak-free sealing engagement between the medical instrument 20, the operational part 21 and/or the proximal end 24, thereby providing a hermetically closed cleaning cavity in which the operational part 21 can be thoroughly cleaned and/or sterilized by introducing a cleaning and/sterilizing agent through the fluid coupling element 12.

The sealing engagement between the sealing member 13 and the medical instrument 20 may be facilitated through the screw coupling 14 as depicted in FIGS. 1 to 5, thus in an embodiment wherein the protection element 2 and cleaning assist element 6 are attached using a screw coupling 14. The screw coupling 14 allows a controlled longitudinal displacement of the cleaning assist element 6 within the cavity 4 by a suitably chosen screw thread. Through rotation the cleaning assist element 6 and the sealing element 13 can be brought into firm contact with the medical instrument 20 and proximal end 24 thereof.

In an alternative embodiment, the protection element 2 and cleaning assist element 6 are attached using a bayonet coupling. The bayonet coupling allows fast insertion of the cleaning assist element 6 into the cavity 4 and through a simple rotation provide a releasable locking engagement between the cleaning assist element 6 and the protection element 2. The bayonet coupling may also facilitate sealing engagement of the sealing member 13 with the medical instrument 20, wherein a simple rotation of the cleaning assist element 6 allows the bayonet coupling to engage and provide sufficient pressure of the sealing element 13 onto the medical instrument 20, in particular the proximal end 24, for obtaining a leak-free connection.

For example, in an embodiment the wall 5 of the protection element 2 may comprises a guiding slot for cooperative engagement with a bayonet pin 17 of the cleaning assist element 6. In the embodiment of FIG. 6 the cleaning assist element 6 comprises a radially outward projecting member to be received in a corresponding guiding slot in the wall 5 of the protection element 2. The outward projecting member may be seen as the bayonet pin 17, which can be moved through the longitudinal slit 11 or cutout 11, see e.g. FIG. 1, as the cleaning assist element 6 is moved through the cavity 4.

In order to facilitate rotation of the cleaning assist element 6 within the cavity 4 of the protection element 2, the cleaning assist element 6 may comprise an outwardly projecting flange portion such as a rim 16 for rotating the cleaning assist element 6, e.g. in clockwise or counter clockwise fashion. Note that the rim 16 can be used for both a screw coupling and/or a bayonet coupling as mentioned above, wherein a rotation of the cleaning assist element 6 allows, for example, the sealing element 13 to be pushed against the medical instrument 20, in particular the proximal end 24, for providing adequate sealing engagement. In a further embodiment the outwardly projecting flange portion 16 or rim 16 is positioned adjacent to the fluid coupling element 12.

In a further embodiment, see e.g. FIGS. 2 and 3, the cleaning assist element 6 may comprise twist extensions 15, which also facilitate rotating the cleaning assist element 6 within the cavity 4 for longitudinal movement there through, so that adequate sealing engagement between the medical instrument 20 and the cleaning assist element 6 can be obtained. In a further embodiment, the twist extensions 15 may comprise one or more circumferentially arranged projecting members positioned adjacent to the fluid coupling element 12.

The present invention embodiments have been described above with reference to a number of exemplary embodiments as shown in the drawings. Modifications and alternative implementations of some parts or elements are possible, and are included in the scope of protection as defined in the appended claims.

The invention claimed is:

1. An assembly for protective storage and cleaning a medical instrument having an operational part and a hand grip part, the assembly comprising:
   a protective storage element having cooperating retention parts for fixing the hand grip part of the medical instrument in the protective storage element;
   a cavity formed by a wall for enclosing at least in part the operational part of the medical instrument; and
   a cleaning assist element having a tubular shape and being fixable to a wall of the protective storage element, wherein
   the retention parts comprise a fixing holder for a distal end of the hand grip part of the medical instrument, and a clamping element for a proximal end of the hand grip part, the hand grip part being receivable between the fixing holder and the clamping element.

2. The assembly of claim 1, wherein the cavity is a cylindrical cavity with a longitudinal axis.

3. The assembly of claim 2, wherein the cavity comprises a longitudinal slit.

4. The assembly of claim 1, wherein the cleaning assist element comprises a fluid coupling element.

5. The assembly of claim 4, wherein the fluid coupling element comprises a tube coupling.

6. The assembly of claim 4, wherein the fluid coupling element is a Luer fitting.

7. The assembly of claim 1, wherein the cleaning assist element comprises a sealing element, which is arranged to seal the operational part of the medical instrument inside the cleaning assist element during operation.

8. The assembly of claim 1, wherein the protective storage element and the cleaning assist element are attached using a screw coupling.

9. The assembly of claim 8, wherein the screw coupling has screw threads having a pitch that determines a linear distance and thus an insertion depth over which the cleaning assist element travels in one revolution.

10. The assembly of claim 1, wherein the protective storage element and the cleaning assist element are attached using a bayonet coupling.

11. The assembly of claim 1, wherein the wall of the protective storage element comprises a guiding slot for cooperative engagement with a bayonet pin of the cleaning assist element.

12. The assembly of claim 1, wherein the cleaning assist element comprises an outwardly projecting flange portion or rim operable for rotating of the cleaning assist element.

13. The assembly of claim 1, wherein the cleaning assist element comprises twist extensions.

14. The assembly of claim 1, wherein the medical instrument is a vitreoretinal forceps.

15. The assembly of claim 1, wherein the cavity is congruent with the cleaning assist element having the tubular shape.

16. The assembly of claim 1, wherein the medical instrument is a multiple procedure medical instrument.

17. The assembly of claim 1, wherein the cleaning assist element comprises an O-ring.

* * * * *